(12) United States Patent
Prais et al.

(10) Patent No.: US 10,113,987 B2
(45) Date of Patent: Oct. 30, 2018

(54) WASHABLE ANALYTE METERS, SEALED CONNECTORS, AND METHODS OF MANUFACTURING AND USING SAME

(71) Applicant: ASCENSIA DIABETES CARE HOLDINGS AG, Basel (CH)

(72) Inventors: Eugene Prais, West Milford, NJ (US); David Huang, Bronx, NY (US); James A. Johnson, Danbury, CT (US); Igor Gofman, Croton-on-Hudson, NY (US); Jun Chen, Warren, NJ (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 292 days.

(21) Appl. No.: 14/911,714

(22) PCT Filed: Aug. 11, 2014

(86) PCT No.: PCT/US2014/050605
§ 371 (c)(1),
(2) Date: Feb. 11, 2016

(87) PCT Pub. No.: WO2015/023611
PCT Pub. Date: Feb. 19, 2015

(65) Prior Publication Data
US 2016/0202205 A1    Jul. 14, 2016

Related U.S. Application Data

(60) Provisional application No. 61/864,958, filed on Aug. 12, 2013.

(51) Int. Cl.
*G01N 27/327*    (2006.01)
*B08B 3/04*    (2006.01)
(Continued)

(52) U.S. Cl.
CPC ....... *G01N 27/3273* (2013.01); *A61B 5/1468* (2013.01); *A61B 5/14532* (2013.01);
(Continued)

(58) Field of Classification Search
CPC ....... H01R 4/60; H01R 43/14; G01N 27/3273
See application file for complete search history.

(56) References Cited

U.S. PATENT DOCUMENTS 5,989,917 A * 11/1999 McAleer ............... B01L 99/00
422/403
2003/0100821 A1    5/2003 Heller et al.
(Continued)

FOREIGN PATENT DOCUMENTS

CN    1735375 A    2/2006
CN    101040185    9/2007
(Continued)

OTHER PUBLICATIONS

International Preliminary Report on Patentability and Written Opinion of International Application No. PCT/US14/50605 dated Feb. 25, 2016.
(Continued)

*Primary Examiner* — Alexander S Noguerola
(74) *Attorney, Agent, or Firm* — Dugan & Dugan, PC

(57) ABSTRACT

An analyte meter to detect an analyte concentration level in a bio-fluid sample may be cleaned and disinfected with a cleaning liquid without harming electrical and internal meter components. In some embodiments, the analyte meter is washable and immersable and may include a sealed sensor connector, sealed battery connector, and possibly a sealed USB connector that may be subjected to a cleaning liquid without the liquid entering an internal chamber of the analyte meter and contacting internal electronic components. In some embodiments, a sealed display screen and
(Continued)

sealed keypad are provided such that liquids are prevented from entering the internal chamber. Manufacturing methods and systems utilizing the analyte sensors are provided, as are numerous other aspects.

21 Claims, 14 Drawing Sheets

(51) Int. Cl.
  *H01R 13/52* (2006.01)
  *H01R 43/14* (2006.01)
  *A61B 5/145* (2006.01)
  *A61B 5/1468* (2006.01)

(52) U.S. Cl.
  CPC ............... *B08B 3/04* (2013.01); *H01R 13/52* (2013.01); *H01R 43/14* (2013.01); *A61B 2560/0214* (2013.01); *A61B 2560/0443* (2013.01); *A61B 2562/227* (2013.01)

(56) References Cited

U.S. PATENT DOCUMENTS

| | | | |
|---|---|---|---|
| 2003/0184264 A1 | 10/2003 | Bertness | |
| 2006/0091006 A1* | 5/2006 | Wang | A61B 5/1486 204/403.02 |
| 2010/0094110 A1* | 4/2010 | Heller | A61L 5/14532 600/345 |
| 2012/0100601 A1 | 4/2012 | Simmons et al. | |
| 2012/0252133 A1 | 10/2012 | Faulkner et al. | |

FOREIGN PATENT DOCUMENTS

| | | |
|---|---|---|
| JP | 2003-513279 | 4/2003 |
| JP | 2004-520898 | 7/2004 |
| JP | 2011-528437 | 11/2011 |
| WO | WO 2015/022299 | 2/2015 |

OTHER PUBLICATIONS

International Search Report and Written Opinion of International Application No. PCT/US14/50605 dated Jan. 22, 2015.
Taiwan Search Report of Taiwan Application No. 103127495 dated Dec. 28, 2017.
Chinese Search Report of Chinese Application No. 201480044785.0 dated Jan. 22, 2018.
Japanese Office Action of Japanese Application No. 2016-534780 dated May 28, 2018.

* cited by examiner

WASHABLE ANALYTE METERS, SEALED CONNECTORS, AND METHODS OF MANUFACTURING AND USING SAME

RELATED APPLICATIONS

The present application claims priority to U.S. Provisional Patent Application No. 61/864,958 filed Aug. 12, 2013, and entitled "WASHABLE ANALYTE METERS, SEALED CONNECTORS, AND METHODS OF MANUFACTURING AND USING SAME" which is hereby incorporated herein by reference in its entirety for all purposes.

FIELD

The invention relates to analyte meters that may be used to detect an analyte concentration level in a bio-fluid sample, analyte sensor electrical connectors, and methods of using and manufacturing thereof.

BACKGROUND

The monitoring of analyte concentration levels in a bio-fluid may be an important part of health diagnostics. For example, an electrochemical analyte sensor may be employed with an analyte meter for monitoring a patient's blood glucose level as part of diabetes treatment and care. Other types of analytes may be measured as well. An electrochemical analyte sensor may be employed, for instance, for detecting an analyte concentration level in a bio-fluid sample, such as from a single sample of blood or other interstitial fluid. The bio-fluid may be obtained from the patient using a lancet (e.g., by a pinprick or needle). Typically, after a bio-fluid sample has been obtained, the sample may then be transferred to an analyte sensor (e.g., typically an analyte sensor strip) for measurement of the bio-fluid sample's analyte concentration level (e.g., a glucose analyte level).

As part of the process, electrodes formed on the analyte sensor are placed in electrical contact with an electrical connector of the analyte meter. Typically, the analyte sensor (e.g., sensor strip) is inserted into a sensor port of the sensor connector. However, portions of the sensor connector housing may be partially open to the inside of the analyte meter and the electrical connection takes place within the interior of the analyte meter. Once the connection is established, the bio-fluid is applied to a receiving end of the sensor strip and the analyte measurement is carried out. During this process, bio-fluids such as blood may contaminate portions of the outside of the meter, such as near the port. Further, the port and the internal electrical connections may become contaminated.

Accordingly, there is a need to provide an analyte meter configured for bio-fluid analyte testing that may overcome certain issues due to contamination.

SUMMARY

In a first aspect, an analyte meter is provided. The analyte meter includes an analyte sensor electrical connector having a sensor port configured to receive an analyte sensor in a port entryway, and at least one wash port coupled to the sensor port and separate from the port entryway, the at least one wash port configured to receive a cleaning fluid.

In another aspect, another analyte meter is provided. The analyte meter includes a meter housing having a first part and a second part interfacing with each other to form an internal chamber, an electronic circuit within the internal chamber, and an analyte sensor electrical connector including a sealed electrical connection through the first part or the second part into the internal chamber, a sensor port configured to receive an analyte sensor in a port entryway, and at least one wash port coupled to the sensor port and separate from the port entryway, the at least one wash port configured to receive a cleaning fluid.

In a method aspect, a method of cleaning an analyte meter is provided. The method includes providing an analyte meter having a sensor port configured to receive an analyte sensor, the sensor port having a port entryway and a wash port, and flowing a cleaning fluid through the wash port to clean the sensor port.

In another method aspect, a method of manufacturing an analyte meter is provided. The method includes providing an analyte meter housing having an internal chamber, providing an analyte sensor electrical connector having at least two electrodes, providing an analyte meter battery connector, forming a sealed connection between the analyte sensor electrical connector and the internal chamber, and forming a sealed connection between the analyte meter battery connector and the internal chamber.

In another aspect, another analyte meter is provided. The analyte meter includes a meter housing having a first part and a second part interfacing with and sealed to one another to form an internal chamber, an electronic circuit within the internal chamber, a sensor port configured to receive an analyte sensor in a port entryway, an analyte sensor electrical connector in the sensor port including a sealed electrical connection through the first part or the second part into the internal chamber, a screen display sealed to one of the first part and a second part, a keypad sealed to one of the first part and a second part, and a removable battery pack including a sealed electrical connection through the first part or the second part into the internal chamber.

In another aspect, another analyte meter is provided. The analyte meter includes a display screen, a keypad, an analyte sensor port, and battery pack interfacing with an electronic circuit located in an internal chamber of a meter housing wherein the internal chamber is entirely sealed and liquid impermeable such that the analyte meter is washable and immersable.

Still other aspects, features, and advantages of the invention may be readily apparent from the following detailed description wherein a number of example embodiments and implementations are described and illustrated, including the best mode contemplated for carrying out the invention. The invention may also be capable of other and different embodiments, and its several details may be modified in various respects, all without departing from the scope of the invention. Accordingly, the drawings and descriptions are to be regarded as illustrative in nature, and not as restrictive. The invention covers all modifications, equivalents, and alternatives falling within the scope of the invention.

BRIEF DESCRIPTION OF THE DRAWINGS

The drawings, described below, are for illustrative purposes only and are not necessarily drawn to scale. The drawings are not intended to limit the scope of the invention in any way.

DESCRIPTION

Reference will now be made in detail to the example embodiments of this disclosure, which are illustrated in the accompanying drawings. Wherever possible, the same reference numbers will be used throughout the drawings to refer to the same or like parts.

Certain regulatory requirements regarding cleaning and disinfection efficacy in a clinical setting are becoming more stringent. Moreover, in cases of high levels of contamination, the analyte measurement itself taken by an analyte meter may be adversely affected because the electrical connection between the analyte (e.g., an analyte sensor strip) and one or more electrodes of the electrical connector may be contaminated or adversely affected in some way.

In view of this concern, embodiments of the invention may provide an entirely hermetically sealed analyte meter that may be washable and, in some embodiments, may even be immersed in a liquid without damage. Accordingly, the sealed analyte meter may be washed in a washing fluid, such as a disinfecting liquid, or the like. In one or more embodiments, the one or more electrical connections of the analyte meter may be sealed. Some may be washable, such as, e.g., the analyte sensor port. Other electrical connections may be sealed and/or washable and/or removable such as a communication connector (e.g., a universal serial bus (USB) port) and/or a battery connection. In some embodiments, the analyte meter itself is entirely washable and all connections thereof may be sealed and washable, including the sensor port, enabling electrical connection with an analyte sensor.

The analyte meter, in accordance with one or more embodiments, may be used to measure any number of analytes, such as glucose, fructose, lactate, keytone, microalbumin, bilirubin, total cholesterol, uric acid, lipids, triglyceride, high density lipoprotein (HDL), low density lipoprotein (LDL), hemoglobin Alc, and the like. These analytes may be detected in, for example, whole blood, blood serum, blood plasma, interstitial fluid, urine, etc. Other types of analytes may be measured provided a suitable reagent exists.

These and other embodiments of washable analyte meters, washable analyte sensor electrical connectors, and methods of using and manufacturing and using the analyte meter are described below with reference to FIGS. 1A-21.

Figure 1A:
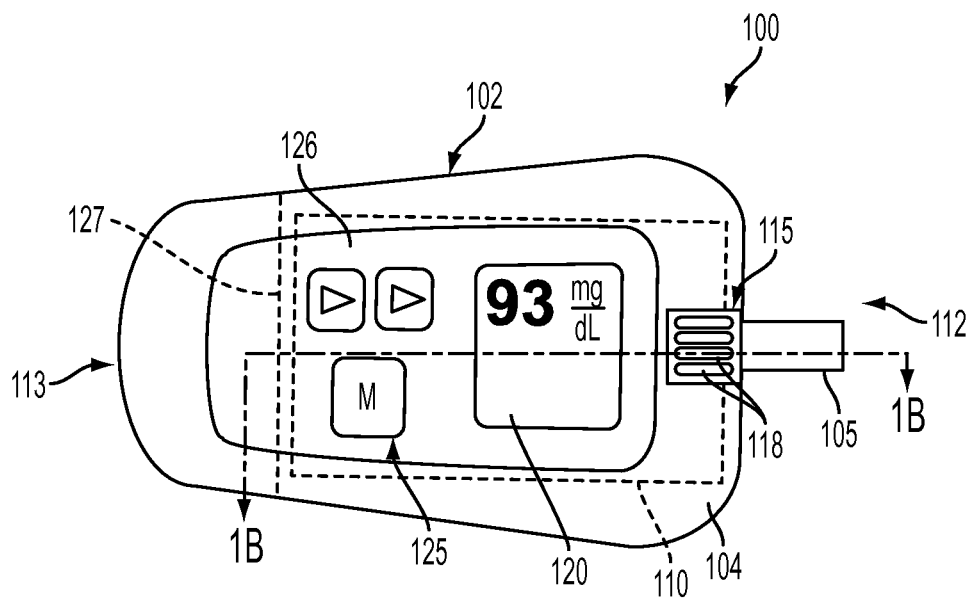
FIG. 1A illustrates a top plan view of a washable analyte meter including a washable sensor connector according to embodiments.
Figure 1B:
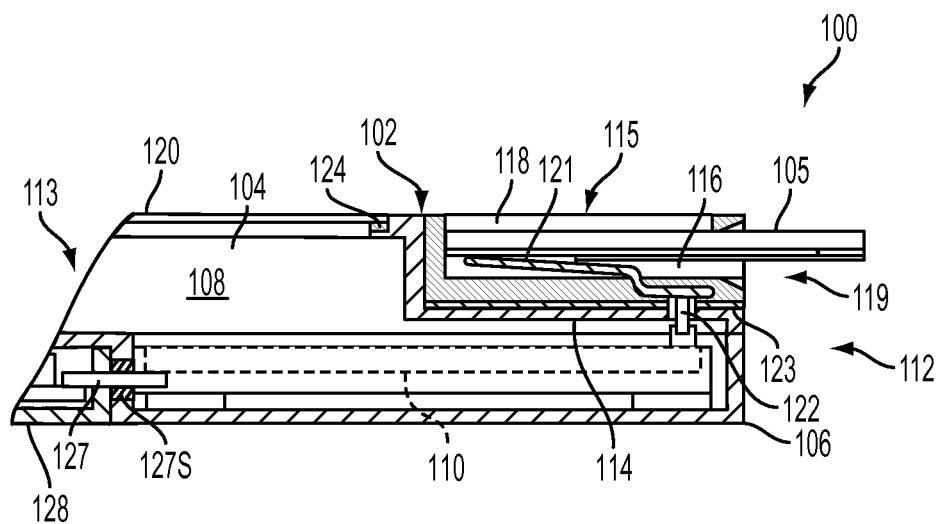
FIG. 1B illustrates a partial cross-sectioned side view of the analyte meter of FIG. 1A taken along section line "1B-1B."
Figure 1C:
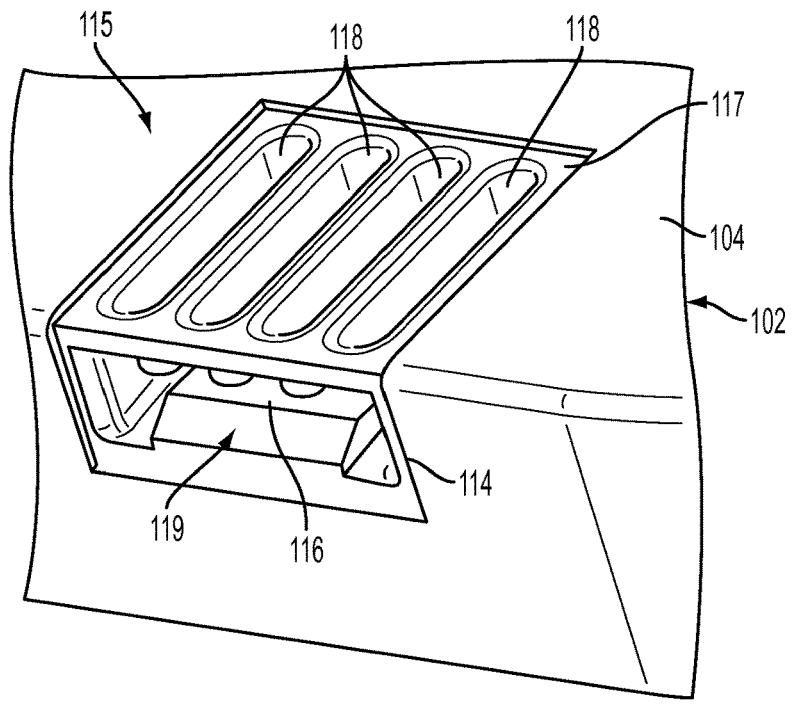
FIG. 1C illustrates a partial perspective view of the washable analyte meter including the washable sensor connector according to embodiments.
Figure 1D:
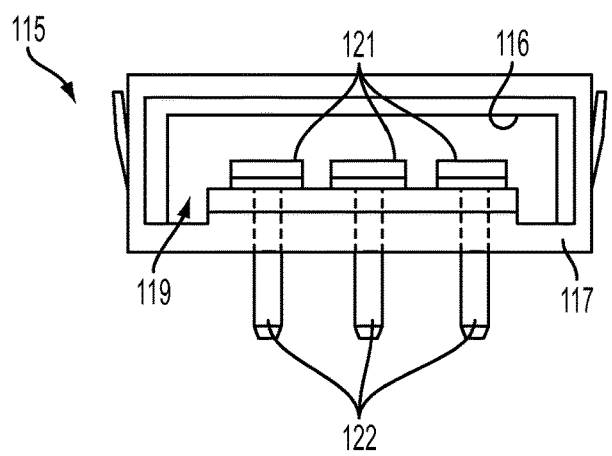
FIG. 1D illustrates a front view of the washable sensor connector of FIG. 1C, shown in isolation.
Figure 1E:
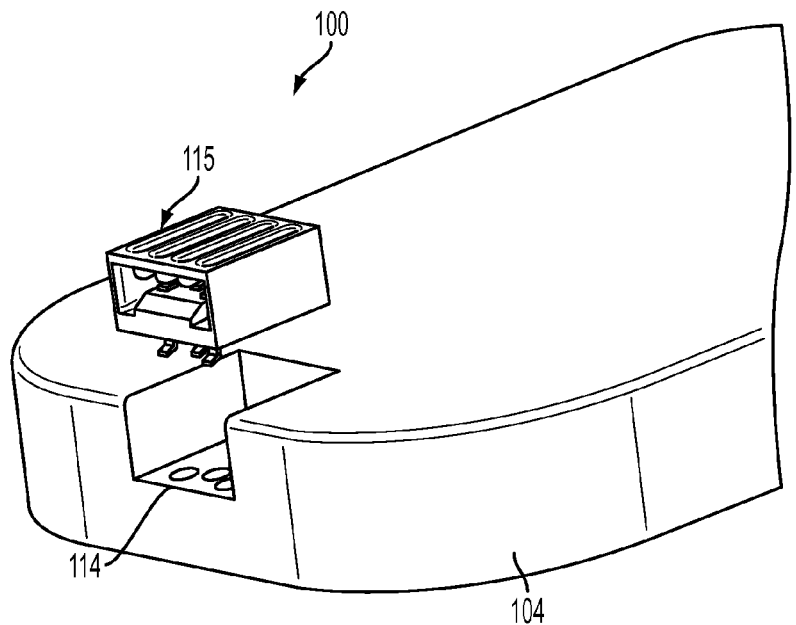
FIGS. 1E-1H illustrates various perspective views of certain components of the washable analyte meter including the washable sensor connector according to embodiments.
Figure 1F:
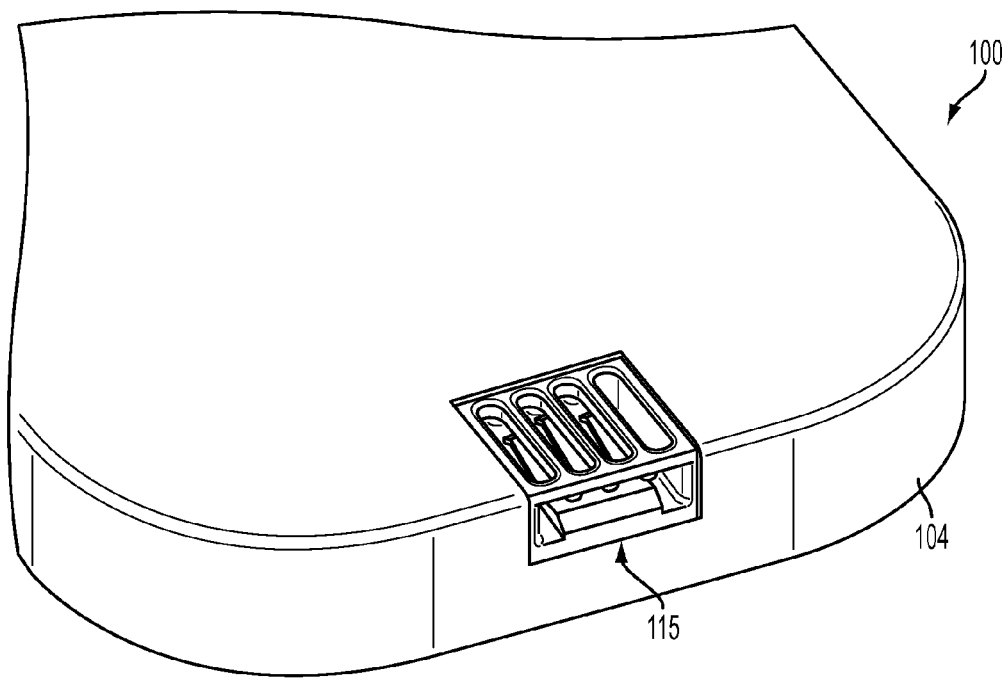
Figure 1G:
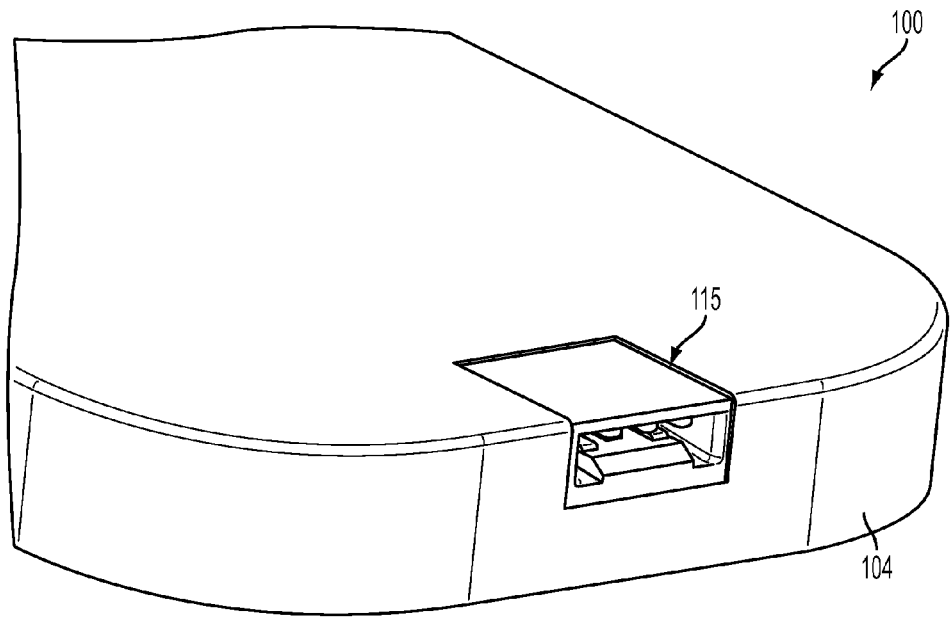
Figure 1H:
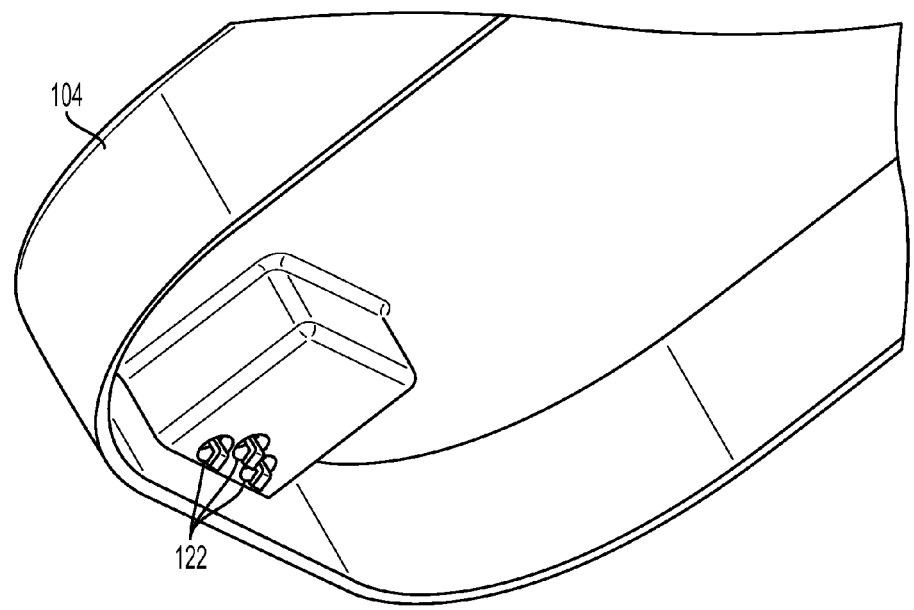

FIGS. 1A-1D illustrates various views of a first example of an analyte meter 100 that is washable according to one or more embodiments. The analyte meter 100 may include a meter housing 102 that may be made of two parts, such as first part 104 and second part 106 that engage each other to form an internal chamber 108 (FIG. 1B). The internal chamber 108 may be configured to contain various internal components of the analyte meter 100, such as a printed circuit board 110 (shown dotted in FIG. 1A), which may contain all or part of an internal electronic circuit. Internal chamber 108 may be entirely sealed and liquid impermeable such that the analyte meter 100 is washable and immersable. The first part 104 and second part 106 may be sealed to each other at their contact surfaces in order to form the internal chamber 108 as a sealed chamber that is sealed from the outside environment. Internal chamber 108 may be hermetically sealed. The first part 104 and second part 106 of the meter housing 102 may be formed of an insulating material such as plastic injection-molded pieces, for example. Sealing may be provided by ultrasonic welding of the first part 104 and second part 106, or by providing a sealant (e.g., a curable sealant), o-ring, gasket, or the like between the first part 104 and the second part 106. Other suitable sealing methods may be used. Connection of the first part 104 to the second part 106 may be made by screws, rivets, snap fit connectors molded on the first part 104 and second part 106, or the like when using a sealant, o-ring, gasket, or the like.

The printed circuit board 110 may reside within the confines of the internal chamber 108. The printed circuit board 110 may include conventional electronic components such as a power supply, processor, memory, and the like that are conventional for carrying out analyte measurements and display thereof. The printed circuit board 110 may be retained in a defined position within the internal chamber 108 by projections and/or recesses formed in one or both of the first part 104 and second part 106. Other suitable positioning features may be used.

The meter housing 102 may have a first end 112 and a second end 113 opposite the first end 112. The first end 112 may include an analyte sensor electrical connector 115 that is fully washable having a sensor port 116 configured to receive an analyte sensor 105 in a port entryway 119 thereof. The analyte sensor electrical connector 115 may also have a one or a plurality of wash ports 118 coupled to sensor port 116 that are separate from port entryway 119. Wash ports 118 may be configured to receive a cleaning fluid there through. The analyte sensor electrical connector 115 may include a connector body 117 that may be received in a recessed pocket 114 of the first part 104 and/or the second part 106. In some embodiments, the connector body 117 of the analyte sensor electrical connector 115 may include a first wall receiving two or more electrodes 121, and a second wall opposite the first wall and including one or more wash ports 118. Two or more electrical connectors 122 may be coupled to two or more electrodes 121 at the first wall. In some embodiments, the two or more electrical connectors 122 may be electrical connector pins. A sealing layer 123 may be provided in some embodiments between a surface of the analyte sensor electrical connector 115 and the first part 104 and/or second part 106, such as in the recessed pocket 114.

In some embodiments, the wash ports 118 may cooperate with the port entryway 119 to form a fluid flow channel enabling flushing of the sensor port 116. The wash ports 118 may be formed through a first wall of the analyte sensor electrical connector 115. As shown best in FIG. 1C, the wash ports 118 may be configured as elongated slots. The wash ports 118 may be one or more in number.

The analyte meter 100 may further include a display screen 120 that may be sealed to the first part 104 and/or second part 106 such that fluids are prevented from entering the internal chamber 108 from between the display screen 120 and the first part 104 and/or second part 106. Similar sealing methods as described above may be used. For example, a sealing material layer 124 may be provided around the periphery of the display screen 120.

The analyte meter 100 may still further include a keypad 125 that may be sealed to the first part 104 and/or second part 106 such that fluids are prevented from entering the internal chamber 108 from between the keypad 125 and the first part 104 and/or second part 106. The seal between the keypad 125 and the first part 104 and/or second part 106 may be provided by employing a thin layer 126 covering over the keys of the keypad 125. The thin layer 126 may be sealed to the first part 104 and/or second part 106 and may be adhered thereto. The thin layer may be a plastic sheet in some embodiments and may include indicia printed or otherwise marked thereon. Other means for sealing the keypad 125 or individual keys may be used.

In some embodiments, the analyte meter 100 may include a battery connector 127 that is sealed to the first part 104 and/or second part 106 such that fluids are prevented from entering the internal chamber 108 from between the battery connector 127 and the first part 104 and/or second part 106. The battery connector 127 allows the use of a removable battery pack 128, as will be described herein.

The analyte meter 100 may also include a universal serial bus (USB) port sealed to the first part 104 and/or second part 106 on a side, for example, such that fluids are prevented from entering the internal chamber 108 from between the USB port and the first part 104 and/or second part 106. Sealed connection for the universal serial bus (USB) port may be the same as for the battery connector 127. A connection seal 127S, such as an elastomer seal, may be provided on the connector or on the first part 104 and/or second part 106 to seal the connection interface.

As further shown in FIGS. 1E-1H and as otherwise described herein, the analyte meter 100 may eliminate any opening allowing liquid ingress into to the internal chamber 108, and may be configured to drain and dry the analyte sensor electrical connector 115 upon washing or cleaning thereof with a cleaning fluid or other liquid. In some embodiments, the analyte sensor electrical connector 115 may be seated within the recessed pocket 114 in the first part 104 of the analyte meter 100. In some embodiments, the electrical connectors may project through one or more apertures in the first part 104 and may be configured to be connected to (e.g., plugged into or otherwise contact) conducting receptacle features on the printed circuit board 110. Other suitable electrical connectors may be used such as bendable leaf spring contacts that contact conducting pads on the printed circuit board 110. In some embodiments, the electrical connectors may be insert-molded in the analyte sensor electrical connector 115 forming a seal between plastic (e.g., the first part 104) and metal. In some embodiments, a sealing layer 123 such as a gasket-type sealing arrangement or other sealing arrangement (sealing compound) may be used between the analyte sensor electrical connector 115 and the surface(s) of the first part 104 and/or second part 106. In some embodiments, the surfaces within the analyte sensor electrical connector 115 may be sloped and/or ventilated as needed to facilitate fluid egress after washing.

Figure 2:
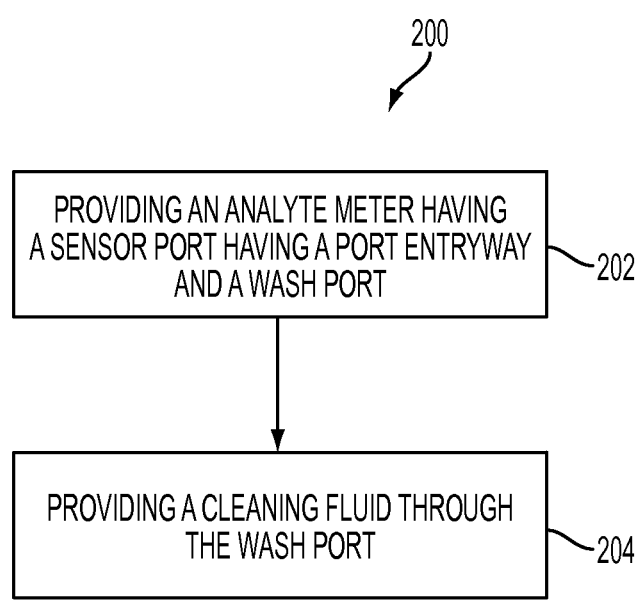
FIG. 2 illustrates a flowchart of a method of using an analyte meter according to embodiments.

FIG. 2 is a flowchart illustrating a method 200 of cleaning an analyte meter in accordance with one or more embodiments. At process block 202, method 200 may include providing an analyte meter (e.g., analyte meter 100) having a sensor port (e.g., sensor port 116) configured to receive an analyte sensor (e.g., analyte sensor 105), the sensor port having a port entryway (e.g., port entryway 119) and a wash port (e.g., wash port 118). At process block 204, method 200 may include flowing a cleaning fluid through the wash port to clean the sensor port. The method 200 of cleaning may be accomplished without adversely affecting the analyte meter.

Figure 3:
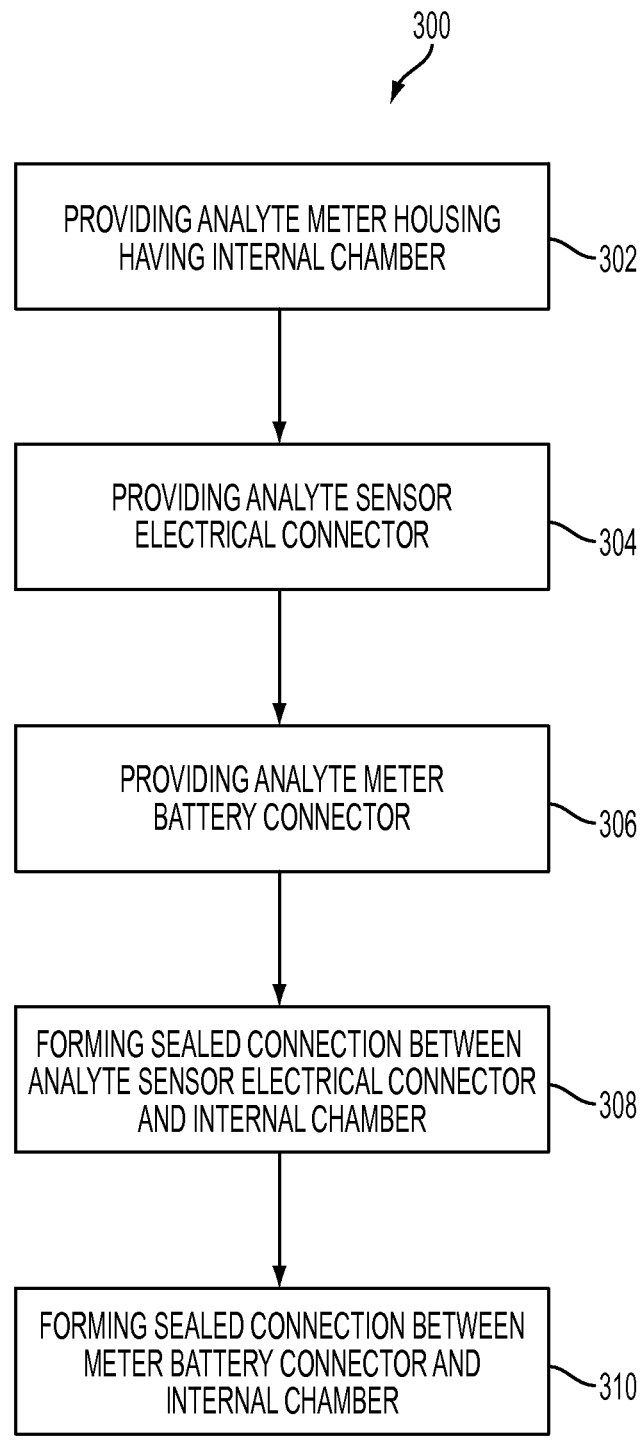
FIG. 3 illustrates a flowchart of a method of manufacturing an analyte meter according to embodiments.

FIG. 3 is a flowchart illustrating a method 300 of manufacturing an analyte meter in accordance with one or more embodiments. At process block 302, method 300 may include providing an meter housing (e.g., meter housing 102) having an internal chamber (e.g., internal chamber 108). At process block 304, method 300 may include providing an analyte sensor electrical connector (e.g., analyte sensor electrical connector 115). The analyte sensor electrical connector may include at least two electrodes (e.g., electrodes 121). Analyte sensor electrical connector 115 may be attachable to the meter housing 102. At process block 306, method 300 may include providing an analyte meter battery connector (e.g., battery connector 127). At process block 308, method 300 may include forming a sealed connection between the analyte sensor electrical connector and the internal chamber. And at process block 310, method 300 may include forming a sealed connection between the analyte meter battery connector and the internal chamber. Any suitable means for accomplishing the sealed connection may be used.

The above process blocks of method 300 may be executed or performed in an order or sequence not limited to the order and sequence shown and described. For example, in some embodiments, process block 304 may be performed after or in parallel with process block 306. Similarly, process block 308 may be performed after or in parallel with process block 310.

Figure 4:
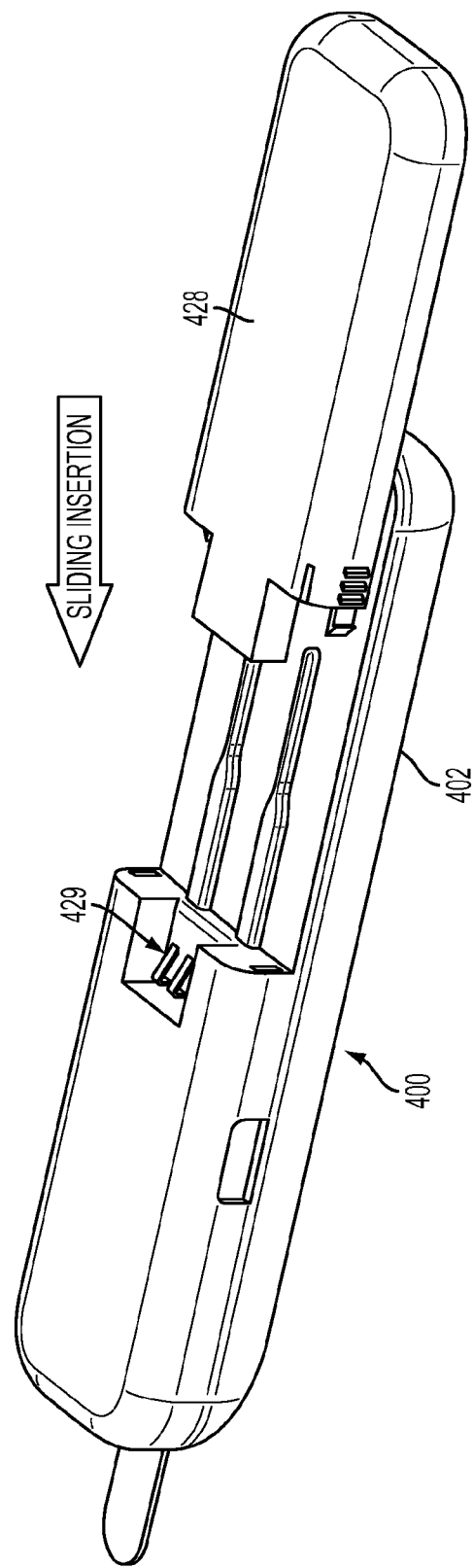
FIGS. 4 and 5 illustrate perspective views of a washable analyte meter including a replaceable battery cartridge according to embodiments.
Figure 5:
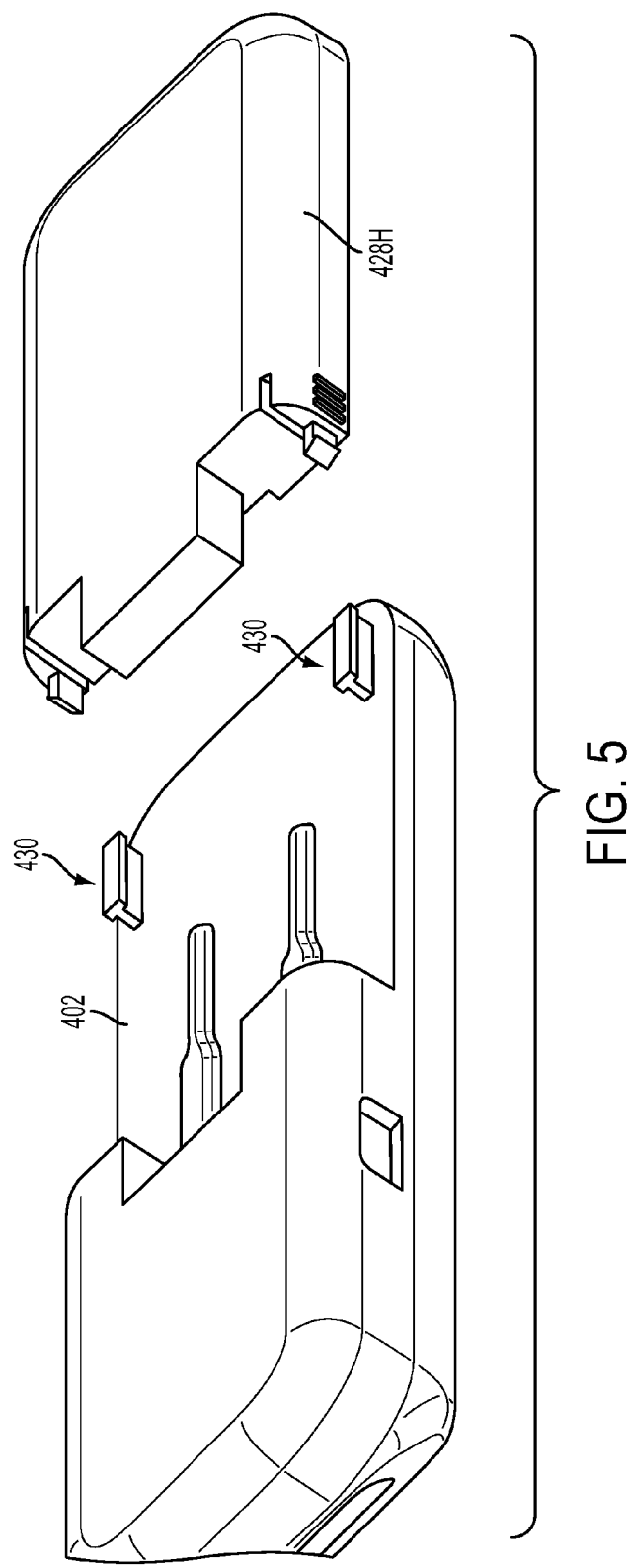
Figure 6:
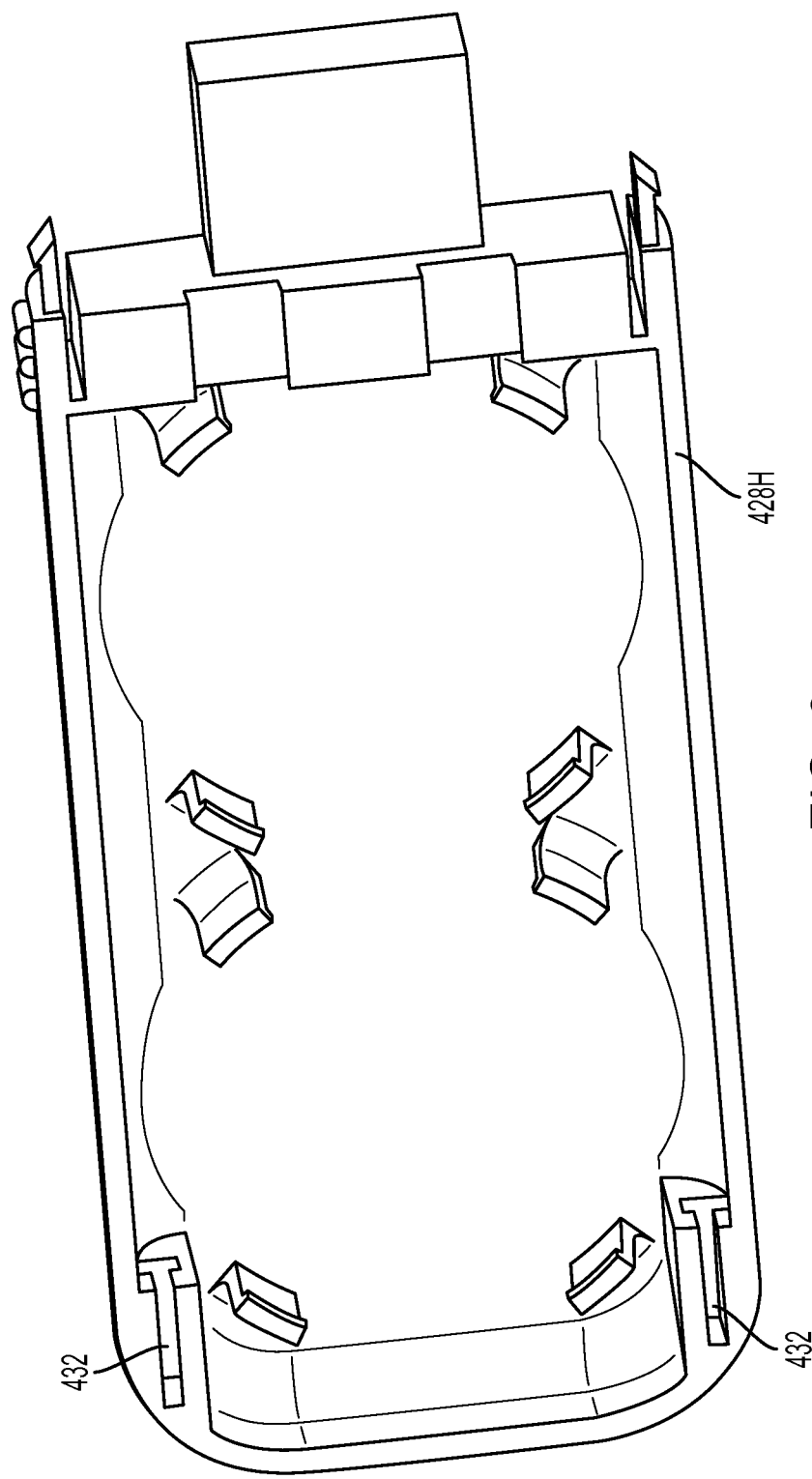
FIGS. 6 and 7 illustrate perspective views of battery cartridge housings according to embodiments.
Figure 7:
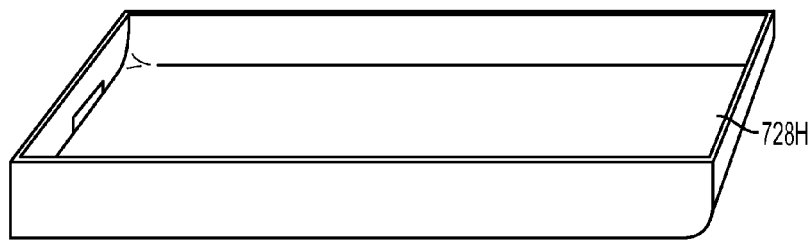

FIGS. 4-6 illustrate an embodiment of a removable or replaceable battery cartridge 428 of an analyte meter 400 that includes a sealed battery connector 429 that may protect against liquid ingress into the internal chamber 108. The sealed battery connector 429 may be provided via the use of a sealed or potted interface in accordance with one or more embodiments. In some embodiments, the replaceable battery cartridge 428 may be configured to attach to an meter housing 402 via slideable insertion.

As shown in FIGS. 5 and 6, some embodiments may include retention features, such as a pair of T-shaped retention rails 430 on opposite sides of a surface of an meter housing 402 (FIG. 5) and a corresponding pair of retention slots 432 in the battery cartridge housing 428H configured to receive the T-shaped rails.

Figure 8:
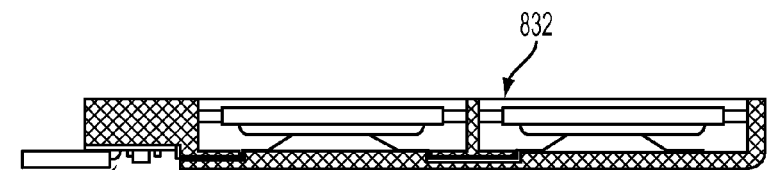
FIGS. 8 and 9 illustrate cross-sectional and top plan views, respectively, of a replaceable battery cartridge according to embodiments.
Figure 9:
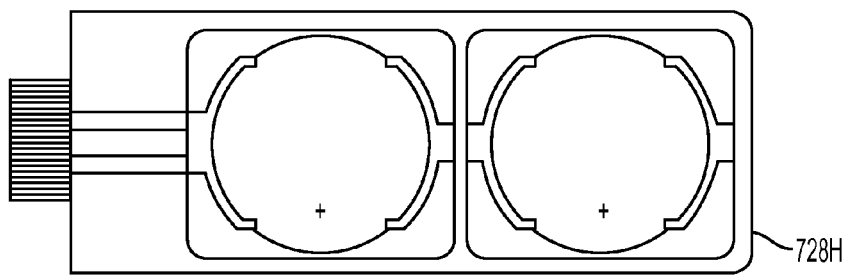
Figure 10:
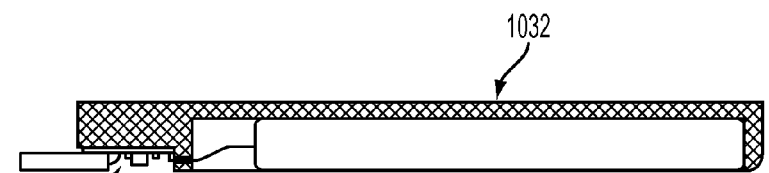
FIGS. 10 and 11 illustrate cross-sectional and top plan views, respectively, of another replaceable battery cartridge according to embodiments.
Figure 11:
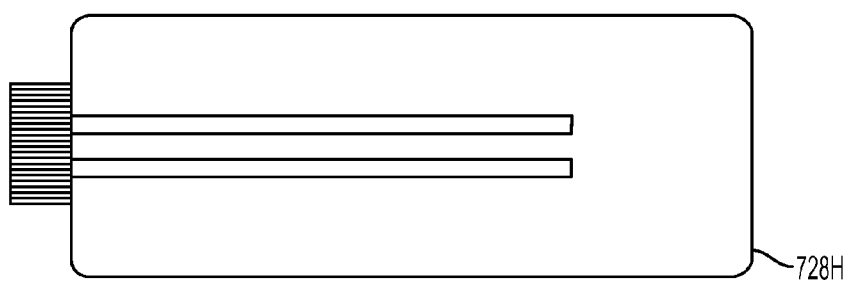

FIGS. 7-11 illustrate a battery cartridge housing 728H (FIG. 7) configured to receive battery cartridge inserts of different battery chemistries in accordance with one or more embodiments. FIGS. 8 and 9 illustrate a battery insert assembly 832 including coin cell batteries and FIGS. 10 and 11 illustrate a battery insert assembly 1032 including a prismatic battery cell, each configured to be inserted in battery cartridge housing 728H.

Figure 12:
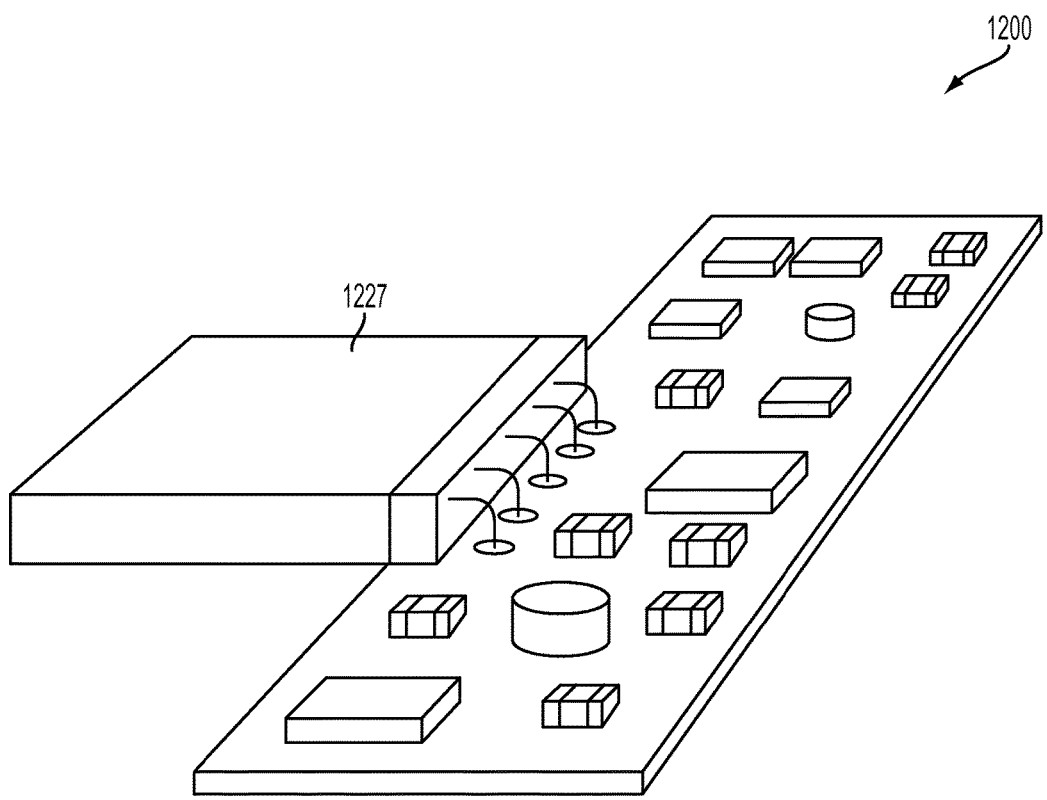
FIG. 12 illustrates a perspective view of a battery cartridge connector and printed circuit board according to embodiments.
Figure 13:
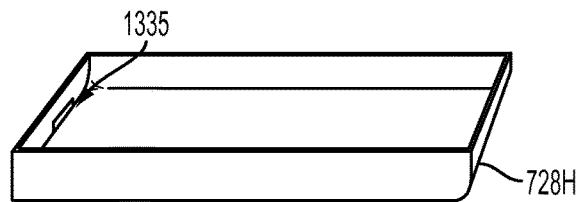
FIG. 13 illustrates a perspective view of a battery cartridge housing according to embodiments.
Figure 14:
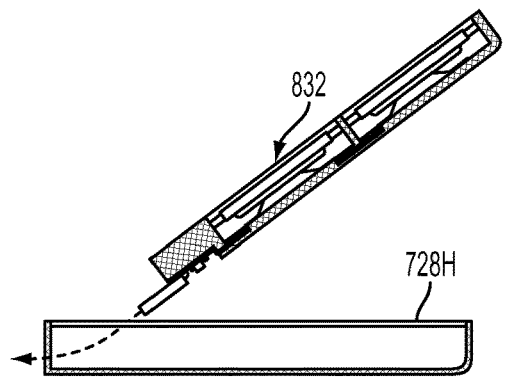
FIGS. 14 and 15 illustrate cross-sectional views of an assembly of a replaceable battery cartridge into the battery cartridge housing of FIG. 13 according to embodiments.
Figure 15:
Figure 16:
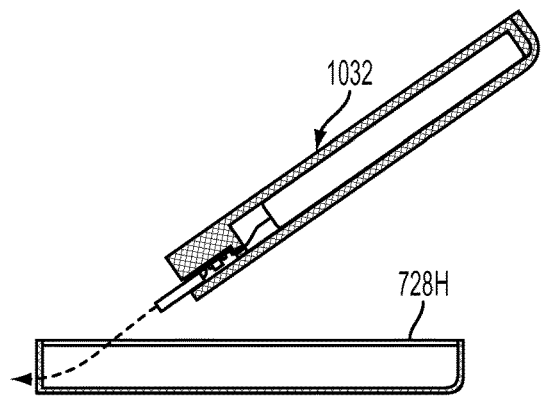
FIGS. 16 and 17 illustrate cross-sectional views of an assembly of another replaceable battery cartridge into the battery cartridge housing of FIG. 13 according to embodiments.
Figure 17:

FIG. 12 illustrates a printed circuit board (PCB) 1200 that may be affixed to the inserts at locations 825 and 1025 (of FIGS. 8 and 10, respectively) in accordance with one or more embodiments. In some embodiments, potting compound may be used to encapsulate the electronics creating a fluid-tight seal (e.g., a water-tight seal). A gasket or potting compound may additionally be used in some embodiments to seal the prismatic battery. Battery electrical connector 1227 extending from the printed circuit board (PCB) 1200 may couple to and provide a sealed connection (e.g., with connection seal 127S) with the meter housing of the analyte meter, for example. Optionally, sealed electrical connectors may be the same as for the analyte sensor electrical connector 115. Thus, power may be readily provided to the analyte meter and the internal chamber 108 may remain entirely hermetically sealed.

As shown in FIGS. 13-17, battery insert assemblies 832, 1032 may be slid into the battery cartridge housing 728H first at an angle such that the interface battery connector slides through an access hole 1335 (see FIG. 13) and then the battery insert assemblies 832, 1032 may be snapped down into the battery cartridge housing 728H. In addition, in some embodiments, the battery insert assembly 832, 1032 may be secured in the battery cartridge housing 728H with potting or an adhesive. In the case of the battery insert assembly 1032 this may also protect the prismatic battery and the battery compartment against liquid ingress.

Embodiments of the battery cartridge housing 728H may allow multiple battery chemistries to be used while maintaining an identical mechanical envelope for an analyte meter (or other suitable battery-powered device). In some embodiments, the electronics in the battery cartridge may be protected against liquid ingress such that the IP22 standard is met. The IP22 standard is part of the Ingress (or International) Protection Rating code published by the International Electrotechnical Commission (IEC). Embodiments of the replaceable battery cartridge may also allow an analyte meter (or other suitable battery-powered device) to meet the IP22 standard for liquid ingress. Embodiments of the replaceable battery cartridges may be user replaceable, thus reducing the cost of replacing a replaceable battery cartridge when the battery/batteries expire(s). In some embodiments, the coin cell batteries of the battery insert assembly 832 of the replaceable battery cartridge may be user replaceable.

Figure 19:
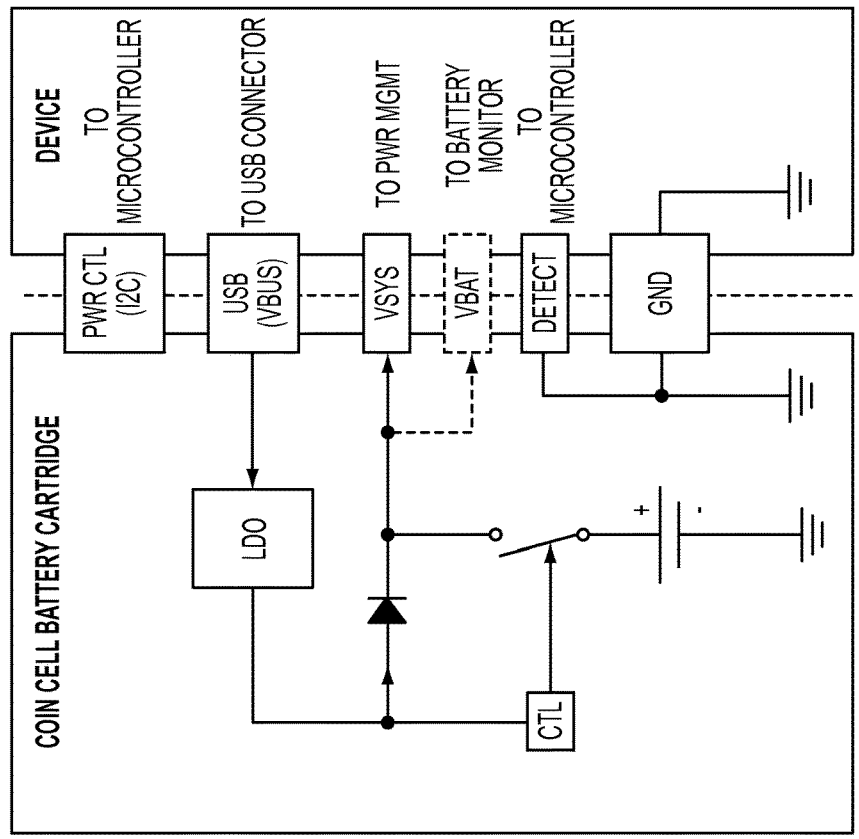
FIGS. 18-21 illustrate schematic circuit diagrams illustrating the electrical connections between a replaceable battery cartridge and an analyte meter according to embodiments.
Figure 18:
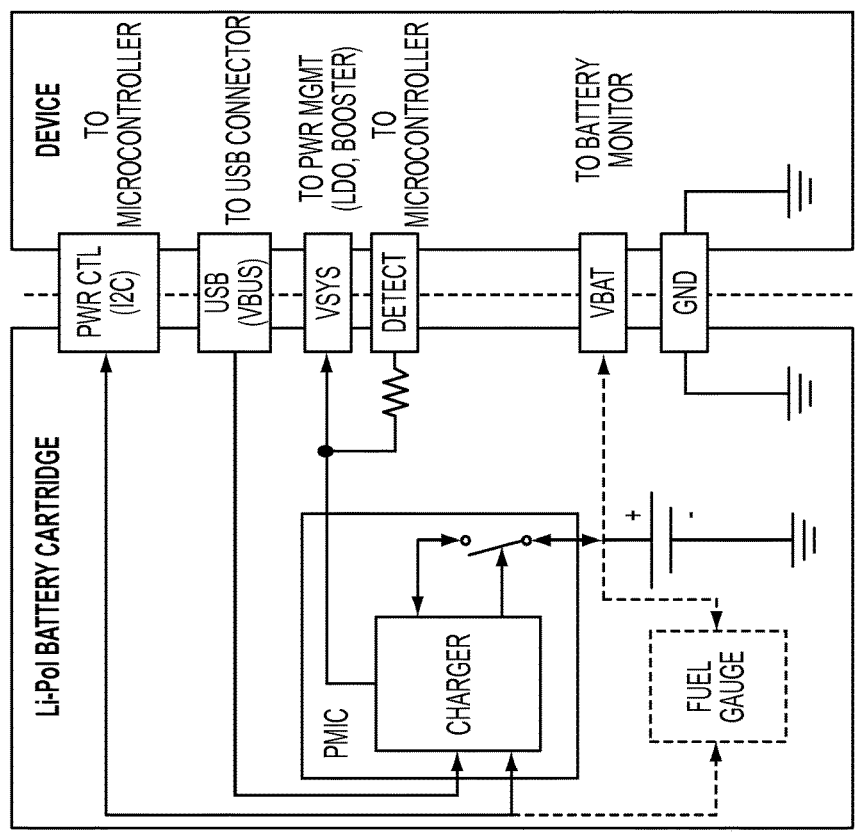
Figure 21:
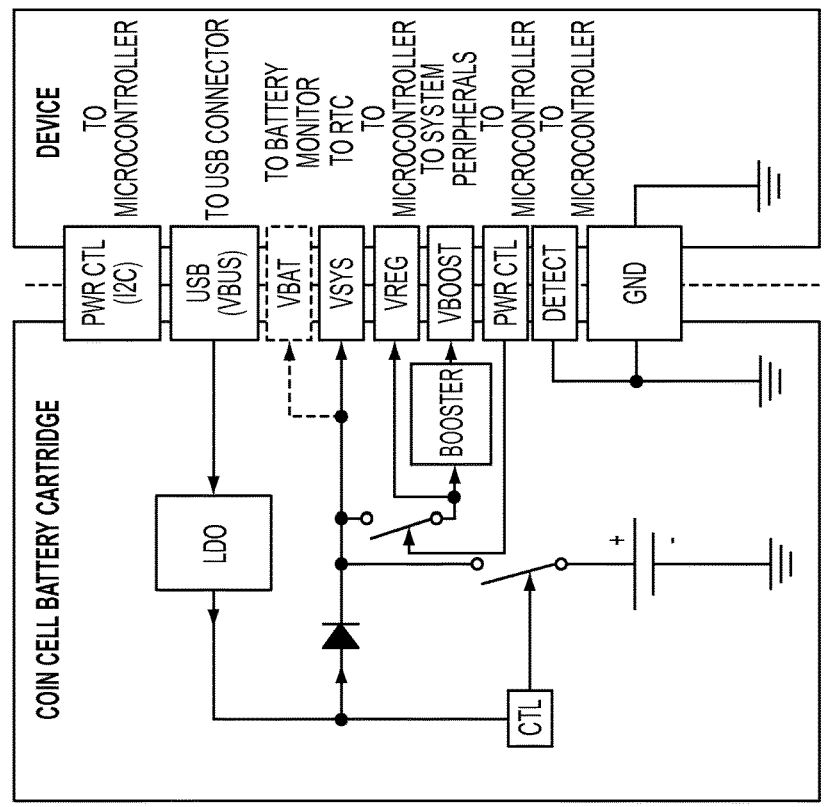
Figure 20:
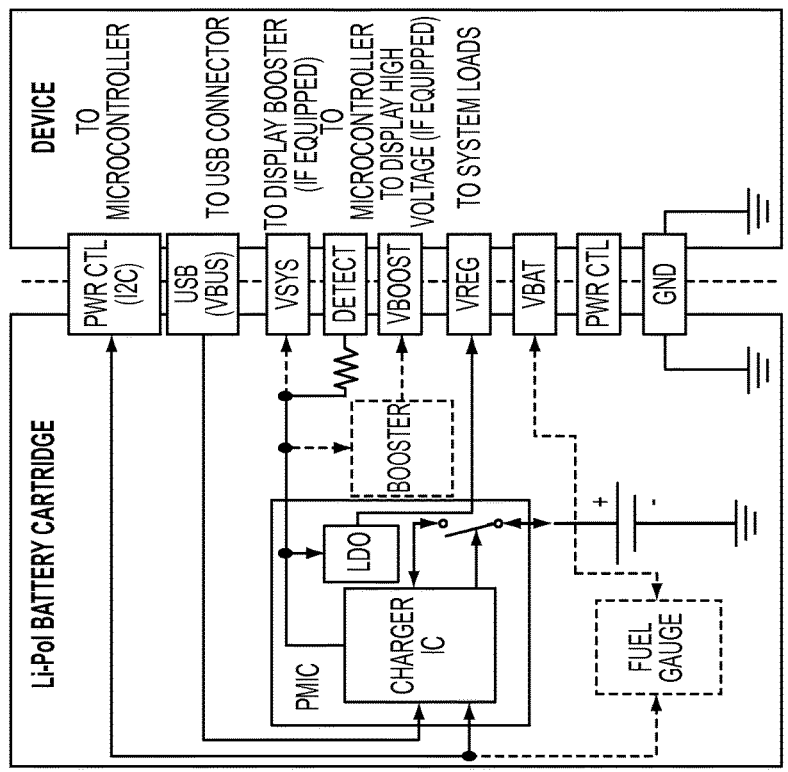

FIGS. 18-21 illustrate the electrical interface between a replaceable battery cartridge and an analyte meter (or other suitable battery-powered device). FIGS. 18 and 19 illustrate less complex circuit topologies of electrical interfaces wherein power management circuitry common to all battery chemistries may be contained in an analyte meter (or other suitable battery-powered device), while the power management circuitry unique to a battery chemistry may be contained in the battery cartridge. FIGS. 20 and 21 illustrate full cartridge electrical interface topologies wherein all power management circuitry may be contained in the battery cartridge.

Accordingly, battery cartridges of different battery chemistries may be mechanically and electrically interchangeable, allowing an analyte meter (or other suitable battery-powered device) to be powered from different battery chemistries.

The foregoing description discloses only example embodiments of analyte meters, sensor connectors, battery cartridges, and methods of manufacturing and using the analyte meters. Modifications of the above-disclosed analyte meters, sensor connectors, and methods, which fall within the scope of the invention, will be readily apparent to those of ordinary skill in the art. Accordingly, while the invention has been disclosed in connection with example embodiments thereof, it should be understood that other embodiments may fall within the scope of the invention, as defined by the following claims.

The invention claimed is:

1. An analyte meter, comprising:
  a meter housing having a first part and a second part interfacing each other to form an internal chamber;
  an analyte sensor electrical connector having a sensor port configured to receive an analyte sensor through a port entryway of the sensor port; and
  at least one wash port coupled to the sensor port and separate from the port entryway, the at least one wash port configured to receive a cleaning fluid;
  wherein the analyte sensor electrical connector includes at least two electrodes at a first wall of the analyte sensor electrical connector, and the at least one wash port is disposed in a second wall opposite the at least two electrodes to facilitate application of the cleaning fluid onto the at least two electrodes and out through the port entryway.

2. An analyte meter, comprising:
  a meter housing having a first part and a second part interfacing each other to form an internal chamber;
  an electronic circuit within the internal chamber; and
  an analyte sensor electrical connector including:
    a sealed electrical connection through the first part or the second part into the internal chamber,
    a sensor port configured to receive an analyte sensor through a port entryway of the sensor port, and
    at least one wash port coupled to the sensor port and separate from the port entryway, the at least one wash port configured to receive a cleaning fluid;
    wherein the analyte sensor electrical connector includes at least two electrodes at a first wall of the analyte sensor electrical connector, and the at least one wash port is disposed in a second wall opposite the at least two electrodes to facilitate application of the cleaning fluid onto the at least two electrodes and out through the port entryway.

3. The analyte meter of claim 2, wherein the first part and the second part comprise a sealed interface forming the internal chamber as a hermetically-sealed internal chamber.

4. The analyte meter of claim 2, wherein the analyte sensor electrical connector comprises a connector body received in a recessed pocket of the first part or second part.

5. The analyte meter of claim 2, wherein the at least one wash port comprises a plurality of wash ports each disposed opposite a respective electrode and having an elongated slot shape.

6. The analyte meter of claim 2, comprising a sealing layer provided between the analyte sensor electrical connector and the first part or the second part.

7. The analyte meter of claim 2, further comprising a display screen sealed to the first part or the second part such that fluids are prevented from entering the internal chamber from between the display screen and the first or second part.

8. The analyte meter of claim 2, further comprising a battery connector sealed to the first part or the second part such that fluids are prevented from entering the internal chamber from between the battery connector and the first or second part.

9. The analyte meter of claim 2, further comprising a universal serial bus port sealed to the first part or the second part such that fluids are prevented from entering the internal chamber from between the universal serial bus port and the first part or second part.

10. An analyte sensor electrical connector, comprising:
a connector body having a first wall, a sensor port having a port entryway configured to receive an analyte sensor, and at least one wash entry configured to receive a cleaning fluid;
two or more electrodes coupled to the first wall; and
two or more electrical connector parts coupled to the two or more electrodes;
wherein the at least one wash entry is disposed in a second wall opposite the two or more electrodes to facilitate application of the cleaning fluid onto the two or more electrodes and out through the port entryway.

11. The analyte sensor electrical connector of claim 10, wherein the at least one wash entry cooperates with the port entryway to form a fluid flow channel enabling flushing of the sensor port.

12. The analyte sensor electrical connector of claim 10 wherein the at least one wash entry is formed as an elongated slot opening through the second wall.

13. The analyte sensor electrical connector of claim 10 wherein the at least one wash entry comprises a plurality of elongated slots.

14. The analyte sensor electrical connector of claim 10 wherein the two or more electrical connector parts comprise connector pins.

15. The analyte sensor electrical connector of claim 10 wherein the connector body includes snap connectors configured to secure the connector body into a pocket of an analyte meter.

16. A method of cleaning an analyte meter, comprising:
providing an analyte meter having a sensor port configured to receive an analyte sensor, the sensor port having a port entryway and a wash port separate from the port entryway; and
flowing a cleaning fluid through the wash port onto electrodes of the sensor port opposite the wash port to clean the sensor port; and
flowing the cleaning fluid out through the port entryway.

17. The method of claim 16, further comprising providing a sealed connection between the sensor port and an internal chamber of the analyte meter.

18. A method of manufacturing an analyte meter, comprising:
providing an analyte meter housing having an internal chamber;
providing an analyte sensor electrical connector having a sensor port and at least two electrodes at a first wall of the analyte sensor electrical connector, the sensor port having a port entryway to receive an analyte sensor there through;
providing at least one wash port coupled to the sensor port, the at least one wash port disposed in a second wall opposite the at least two electrodes to facilitate application of a cleaning fluid onto the at least two electrodes and out through the port entryway;
providing an analyte meter battery connector;
forming a sealed connection between the analyte sensor electrical connector and the internal chamber; and
forming a sealed connection between the analyte meter battery connector and the internal chamber.

19. The method of claim 18, further comprising providing a battery cartridge configured to mechanically and electrically couple to the analyte meter housing and comprising battery chemistry power management circuits.

20. An analyte meter, comprising:
a meter housing having a first part and a second part interfacing with and sealed to one another to form an internal chamber;
an electronic circuit within the internal chamber;
a sensor port configured to receive an analyte sensor through a port entryway of the sensor port;
at least one wash port coupled to the sensor port and separate from the port entryway;
at least two electrodes in the sensor port including a sealed electrical connection through the first part or the second part into the internal chamber, the at least two electrodes at a first wall, and the at least one wash port disposed in a second wall opposite the at least two electrodes to facilitate application of a cleaning fluid onto the at least two electrodes and out through the port entryway;
a screen display sealed to one of the first part and a second part;
a keypad sealed to one of the first part and a second part; and
a removable battery pack including a sealed electrical connection through the first part or the second part into the internal chamber.

21. An analyte meter, comprising:
display screen, keypad, analyte sensor electrical connector, and battery pack interfacing with an electronic circuit located in an internal chamber of a housing body wherein the internal chamber is entirely sealed and liquid impermeable such that the analyte meter is washable and immersible; wherein the analyte sensor electrical connector includes an analyte sensor port that includes a port entryway to receive an analyte sensor there through and has at least one wash port coupled thereto to receive a cleaning fluid there through, wherein the analyte sensor electrical connector further includes at least two electrodes at a first wall of the analyte sensor electrical connector, and the at least one wash port is disposed in a second wall opposite the first wall.

* * * * *